United States Patent [19]

Malhotra et al.

[11] 4,256,893

[45] Mar. 17, 1981

[54] SUBSTITUTED PHENOXY AND PHENYLTHIO PYRIDINE METHANOLS AND SUBSTITUTED METHANOLS

[75] Inventors: Sudarshan K. Malhotra, Walnut Creek; Michael J. Ricks, Martinez, both of Calif.

[73] Assignee: The Dow Chemical Company, Midland, Mich.

[21] Appl. No.: 17,752

[22] Filed: Mar. 5, 1979

Related U.S. Application Data

[63] Continuation-in-part of Ser. No. 859,908, Dec. 12, 1977, Pat. No. 4,163,787, which is a continuation-in-part of Ser. No. 777,188, Mar. 14, 1977, abandoned.

[51] Int. Cl.³ .................. C07D 213/64; C07D 213/70
[52] U.S. Cl. ..................................... 546/301; 424/263; 546/302; 546/303
[58] Field of Search ................ 546/300, 301, 302, 303

[56] References Cited

U.S. PATENT DOCUMENTS 4,163,787  8/1979  Malhotra et al. .................... 546/301

FOREIGN PATENT DOCUMENTS 50-76072  6/1975  Japan ...................... 546/330
50-76073  6/1975  Japan ...................... 546/330

OTHER PUBLICATIONS

Wrobel et al., Chemical Abstracts vol. 64, cols. 15936 (1966) (abst. of Wrobel et al., Roczniki Chem. vol. 39, pp. 1239–1244 (1965).
Provita et al., Chem. Abst. vol. 84, abst. 44146r (1976) (abst. of Czech. Pat. No. 153,855).
Maeda et al., Chemical Abstracts, vol. 84, abst. Nos. 43857m and 43858n (1976) (abst. of Japanese Kokai Nos. 75-76072 and 76073).

*Primary Examiner*—John D. Randolph
*Attorney, Agent, or Firm*—S. Preston Jones; Ronald G. Brookens

[57] ABSTRACT

Substituted phenoxy and phenylthio pyridine methanols and substituted methanols are prepared which correspond to the formula:

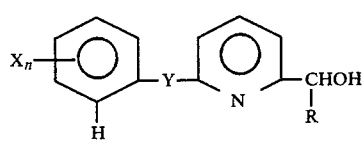

(Formula I)

wherein X independently represents alkyl of 1 to 4 carbon atoms, alkoxy of 1 to 4 carbon atoms, alkylthio of 1 to 4 carbon atoms, alkylsulfonyl of 1 to 4 carbon atoms, trifluoromethyl, 3,4-methylenedioxy, chloro, fluoro or bromo; n represents an integer of 0 to 2; Y represents oxygen or sulfur and R represents hydrogen, cyano or ethynyl. These compounds are employed as intermediates in the preparation of compounds which have a high degree of insecticidal activity.

13 Claims, No Drawings

SUBSTITUTED PHENOXY AND PHENYLTHIO PYRIDINE METHANOLS AND SUBSTITUTED METHANOLS

CROSS-REFERENCE TO RELATED APPLICATION

This is a continuation-in-part of application Ser. No. 859,908, filed Dec. 12, 1977, now U.S. Pat. No. 4,163,787, issued Aug. 7, 1979 which in turn is a continuation-in-part of application Ser. No. 777,188, filed Mar. 14, 1977, now abandoned.

DESCRIPTION OF PRIOR ART

Various insecticidal compounds which are esters of cyclopropane carboxylic acid are known. 3-(Fluorophenoxy)benzyl substituted cyclopropanecarboxylates are taught in German Pat. No. 2,547,534. 3-Phenoxybenzyl cyclopropane carboxylates are also taught in Japanese Pat. No 76-011106. Phenoxy phenyl substituted cyclopropanecarboxylates are taught as insecticides and acaricides in U.S. Pat. No. 3,961,070 and as tick control agents in South African Pat. No. 75/03,211 (based on U.S. patent application Ser. No. 487,417 filed Oct. 7, 1974). Other related substituted phenyl esters of cyclopropane carboxylic acids are taught in French Pat. No. 2,281,918. Various insecticidal 3-(dihalovinyloxy)-benzyl esters of cyclopropanecarboxylic acid are taught in German Pat. No. 2,554,883 and ectoparasites are taught to be controlled by the use of 3-phenoxybenzyl esters of spirocarboxylic acids in U.S. Pat. No. 3,962,458. In addition, U.S. Pat. No. 3,979,519 teaches 3-(2,2-dihalovinyloxy)benzyl 2-(2,2-dihalovinyl) 3,3-dialkylcyclopropane carboxylates as insecticides.

SUMMARY OF THE INVENTION

The present invention is directed to substituted phenoxy and phenylthio methanols and substituted methanols useful in preparing substituted pyridine methyl esters of cyclopropane carboxylic acids corresponding to the formula

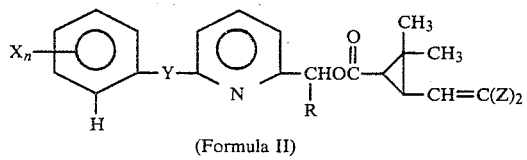

(Formula II)

wherein X independently represents alkyl of 1 to 4 carbon atoms, alkoxy of 1 to 4 carbon atoms, alkylthio of 1 to 4 carbon atoms, alkylsulfonyl of 1 to 4 carbon atoms, trifluoromethyl, 3,4-methylenedioxy, chloro, fluoro or bromo; n represents an integer of 0 to 2; Y represents oxygen or sulfur; R represents hydrogen, cyano or ethynyl and Z represents chloro, fluoro or bromo. These latter compounds are useful in the kill and control of various insect pest and such compounds and their use constitute the subject matter in applicants' Co-pending application Ser. No. 859,908.

In the present specification and claims, the term "alkyl of 1 to 4 carbon atoms" is employed to designate straight chain alkyls of 1 to 4 carbon atoms, branched chain alkyls of 3 or 4 carbon atoms and cyclic alkyls of 3 or 4 carbon atoms such as, for example, methyl, ethyl, propyl, butyl, isopropyl, isobutyl, secondary butyl, tertiary butyl, cyclopropyl and cyclobutyl.

In the present specification and claims, the terms "alkoxy of 1 to 4 carbon atoms", "alkylthio of 1 to 4 carbon atoms" and "alkylsulfonyl of 1 to 4 carbon atoms" are employed to designate alkoxy and alkylthio groups of the formula —Y—loweralkyl wherein Y is oxygen, sulfur or sulfonyl and alkyl is defined as hereinabove set forth for "alkyl of 1 to 4 carbon atoms".

The insecticidal carboxylic acid compounds are generally high boiling liquids and possess low mammalian toxicity. The compounds are substantially insoluble in water and usually are moderately to highly soluble in common organic solvents.

The insecticidal carboxylic acid compounds can be prepared by the reaction of an appropriate substituted phenoxy or phenylthio pyridine methanol or substituted methanol and an appropriate 2,2-dimethyl-3-(2,2,-dihaloethenyl or vinyl)cyclopropane carboxylic acid halide in the presence of a solvent and a hydrogen halide acceptor. The reaction scheme is as follows:

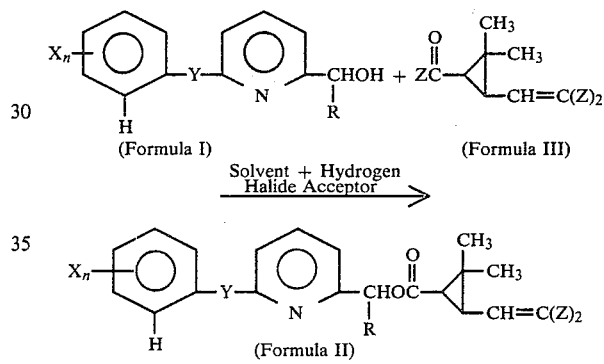

In carrying out this reaction, the appropriate phenoxy or phenylthio pyridine methanol or substituted methanol and the appropriate 2,2-dimethyl-3-(2,2-dihalovinyl)cyclopropane carboxylic acid halide are mixed together in substantially equimolar amounts, with the solvent, conveniently at room temperature. The hydrogen halide acceptor is thereafter added to the above mixture, with stirring. The mixture is stirred for from 0.1 to 24 hours and the mixture is then diluted with water and extracted thoroughly with a conventional solvent such as, for example, diethyl ether, hexane, methylene chloride or chloroform. The solvent extract is water washed, dried and concentrated under reduced pressure and if desired, purified by distillation or other conventional methods.

Representative solvents for use in carrying out this reaction include diethyl ether, methylene chloride, glyme and hexane.

Representative hydrogen halide acceptors include conventional bases such as, for example, triethylamine, pyridine, dimethylaniline and the conventional alkali metal bases such as sodium hydroxide, potassium hydroxide, sodium carbonate, potassium bicarbonate, sodium bicarbonate, and the like.

It should be understood that the various geometric isomers as well as the mixed compound can be prepared by the procedures taught herein.

DESCRIPTION OF SOME PREFERRED EMBODIMENTS

The following examples illustrate the present invention and the manner by which it can be practiced but, as such, should not be construed as limitations upon the overall scope of the same.

The phenoxy or phenylthio pyridine methanol or substituted methanol corresponding to the formula

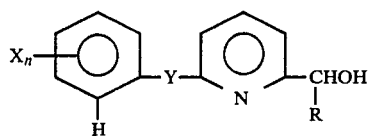

(Formula I)

wherein X, n, Y and R are as hereinbefore defined, can be prepared by a variety of procedures depending upon the R substituent.

For those compounds of Formula I wherein R is hydrogen, the compounds can be prepared by the reaction of an appropriate phenoxy or phenylthio pyridine carboxylic acid methyl ester of the formula

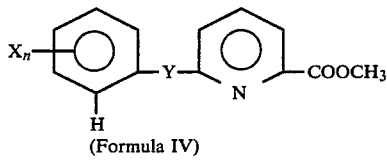

(Formula IV)

wherein X, n, and Y are as hereinbefore defined with sodium borohydride in the presence of a solvent.

In carrying out this reaction, the ester reactant is dissolved in a solvent such as methanol, or ethanol and the mixture cooled to a temperature of from about 0° to about 15° C. The sodium borohydride is thereafter added thereto while the temperature is maintained in the above range. The mixture is maintained under these conditions until gas evolution is complete. Thereafter, the solvent is removed by evaporation and the residue taken up in a solvent such as, for example, diethyl ether. This mixture is water washed, washed with dilute hydrochloric acid (5–10%), dried and the solvent removed by evaporation to give the alcohol product. If desired, the product can be further purified.

EXAMPLE I 6-(phenoxy)picolinalcohol

A solution was prepared by dissolving 5.1 grams (0.022 mole) of 6-(phenoxy)methyl picolinate in ~250 milliliters of methanol. The solution was cooled to 10° C. and 7.6 grams (0.2 mole) of sodium borohydride was added thereto portionwise over 1 hour while the temperature was maintained at ~30° C. Foaming occurred during the addition and when it ceased, the methanol was removed by evaporation. The residue which remained was dissolved in ether and the resulting solution water washed, washed with dilute hydrochloric acid, dried and the solvent removed by evaporation. The tan oil which remained was distilled to give 1.6 grams of 6-(phenoxy)picolinalcohol as an off-white oil. The structure of the product was confirmed by NMR.

By following the preparative procedures as outlined in the above examples, the following compounds set forth in Table I are prepared.

TABLE I

| $X_n$ | Y |
|---|---|
| 3-CH$_3$ | O |
| 2-CH$_3$ | O |
| 4-Cl | O |
| 3-CF$_3$ | S |
| 2-CF$_3$ | S |
| H | S |
| H | O |
| 4-F | O |
| 4-CH$_3$ | O |
| 4-C$_2$H$_5$ | O |
| 3-C$_2$H$_5$ | O |
| 2-C$_2$H$_5$ | S |
| 3-i-C$_3$H$_7$ | S |
| 4-Br | O |
| 2,4-Br$_2$ | S |
| 4-OCH$_3$ | S |
| 2-OCH$_3$ | O |
| 3-OCH$_3$ | O |
| 3-CF$_3$ | O |
| 3-OCH$_3$; 4-OC$_2$H$_5$ | S |
| 2-CF$_3$ | O |
| 3-i-C$_3$H$_7$ | S |
| 2-OC$_4$H$_9$ | O |
| 4-OC$_4$H$_9$ | S |
| 3-CH$_3$; 5-C$_4$H$_9$ | O |
| 2-Cl; 4-Br | S |
| 2-Cl; 4-CF$_3$ | O |
| 3,5-(SCH$_3$)$_2$ | S |
| 4-SCH$_3$ | O |
| 4-SO$_3$CH$_3$ | O |
| 3,5-(OC$_4$H$_9$)$_2$ | O |
| 4-SO$_2$C$_4$H$_9$ | O |
| 3-C$_4$H$_9$ | O |
| 4-SC$_4$H$_9$ | O |
| 3,5-(CF$_3$)$_2$ | S |

The phenoxy or phenylthio pyridine carboxylic acid methyl esters of the formula

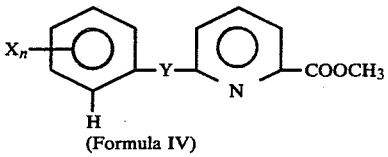

(Formula IV)

wherein X, n, and Y are as hereinbefore defined and employed as starting materials can be prepared by reacting an appropriate substituted phenol or phenyl mercaptan with a slight excess of the methyl ester of 6-chloro picolinic acid in the presence of a base such as an alkali metal hydride or lower alkoxide such as, for example, sodium, potassium, lithium or cesium hydride or sodium, potassium, lithium or cesium lower alkoxide of 1 to 4 carbon atoms (such as, methoxide, ethoxide, n-propoxide, i-propoxide, n-butoxide, sec-butoxide or t-butoxide), and a solvent such as, for example, diglyme, dimethylsulfoxide or dimethylformamide. This reaction can be characterized as follows:

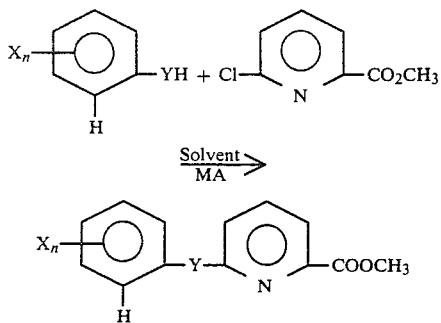

wherein X, n, and Y are as hereinbefore defined and MA is an alkali metal hydride or alkoxide.

In carrying out this reaction, a solution of the phenyl mercaptan or phenol is dissolved in the solvent and the base is slowly added to a solution of the methyl ester dissolved in a solvent at a temperature of from about 100° to about 120° C. After the addition is complete, the temperature is slowly raised to about 130° to about 150° C. The reaction is usually complete in from about 1.5 to about 5.5 hours depending upon the reactants. After the reaction is complete, the reaction mixture is cooled below 70° C. and poured over ice. The product comes down as a solid and is separated by filtration or as an oil and separated by decantation. The crude product is taken up in diethyl ether, washed with water and a base such as, for example, sodium bicarbonate and dried. The solvent is thereafter removed and if desired, the product can be further purified by recrystallization from a solvent such as hexane, benzene, pentane, xylene or by distillation.

EXAMPLE II 6-(6-Fluorophenoxy)methyl picolinate

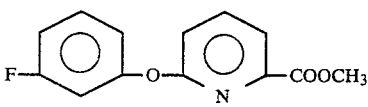

To a solution of 37.7 grams (0.22 mole) of 6-chloromethyl picolinate in 300 milliliters of diglyme was added dropwise a solution comprising 27.2 grams (0.24 mole) of 3-fluorophenol, 27.2 grams (0.24 mole) of potassium t-butoxide in 100 milliliters of diglyme. The addition was carried out at between 120°–130° C. The temperature was slowly raised to 145° C. and after a 2.5 hour reaction time, the reaction was complete. The reaction mixture was cooled to ~70° C. and poured over ice. The solid 6-(6-fluorophenoxy)methyl picolinate which formed was filtered off and dissolved in ether. This solution was washed with water, dilute sodium hydroxide and dried over anhydrous magnesium sulfate and the ether evaporated off. The product which remained as a residue was crystallized from hexane and recovered in a yield of 25.4 grams melting at 54°–55° C. The structure of the compound was confirmed by NMR. Upon analysis, the compound was found to have carbon, hydrogen and nitrogen contents of 62.86, 4.28 and 5.53 percent, respectively, as compared with the theoretical contents of 63.15, 4.08 and 5.67 percent, respectively, calculated for the above-named compound.

By following the preparative procedures as outlined above, employing the appropriate reactants, the following compounds set forth in Table II are prepared.

TABLE II

| $X_n$ | Y |
|---|---|
| 3-CH$_3$ | O |
| 2-CH$_3$ | O |
| H | O |
| H | S |
| 4-Cl | O |
| 3-OCH$_3$ | O |
| 4-SO$_2$CH$_3$ | O |
| 3-CF$_3$ | S |
| 2-CF$_3$ | S |
| 4-F | O |
| 4-CH$_3$ | O |
| 4-C$_2$H$_5$ | O |
| 3-C$_2$H$_5$ | O |
| 2-C$_2$H$_5$ | S |
| 3-i-C$_3$H$_7$ | S |
| 4-Br | O |
| 2,4-Br$_2$ | S |
| 4-OCH$_3$ | S |
| 2-OCH$_3$ | O |
| 3-OCH$_3$; 4-OC$_2$H$_5$ | S |
| 3-CF$_3$ | O |
| 2-Cl; 4-CF$_3$ | O |
| 2-CF$_3$ | O |
| 3-i-C$_3$H$_7$ | S |
| 2-OC$_4$H$_9$ | O |
| 4-OC$_4$H$_9$ | S |
| 3,5-(SCH$_3$)$_2$ | S |
| 4-SCH$_3$ | O |
| 3,5-(OC$_4$H$_9$)$_2$ | O |
| 3-C$_4$H$_9$ | O |
| 4-SC$_4$H$_9$ | O |
| 2-Cl; 4-Br | S |
| 3-CH$_3$; 5-C$_4$H$_9$ | O |
| 3,5-(CF$_3$)$_2$ | S |

For those compounds of Formula I wherein R is —C≡CH, the compounds can be prepared by reacting an appropriate 6-(phenoxy)picolinaldehyde with lithium acetylide, lithium trimethylsilyl bromide or ethynyl magnesium bromide. The reaction can be characterized as follows:

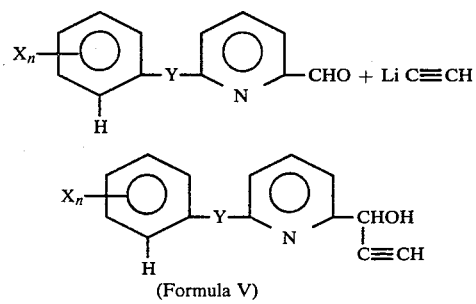

(Formula V)

wherein n, X and Y are as hereinbefore defined.

By following the preparative procedure outlined above, the following compounds set forth in Table III can be prepared.

TABLE III

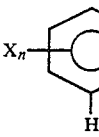

| $X_n$ | Y |
|---|---|
| 3-CH₃ | O |
| 2-CH₃ | O |
| 4-Cl | O |
| H | S |
| H | O |
| 3-CF₃ | S |
| 2-CF₃ | S |
| 4-F | O |
| 2-Cl; 4-Br | S |
| 4-CH₃ | O |
| 4-C₂H₅ | O |
| 3-C₂H₅ | O |
| 2-C₂H₅ | S |
| 3-i-C₃H₇ | S |
| 3-CH₃; 5-C₄H₉ | O |
| 4-Br | O |
| 2,4-Br₂ | S |
| 3-OCH₃; 4-OC₂H₅ | S |
| 4-OCH₃ | S |
| 3-OCH₃ | O |
| 2-OCH₃ | O |
| 3-CF₃ | O |
| 2-CF₃ | O |
| 2-Cl; 4-CF₃ | O |
| 3-i-C₃H₇ | S |
| 2-OC₄H₉ | O |
| 4-OC₄H₉ | S |
| 3,5-(SCH₃)₂ | S |
| 4-SCH₃ | O |
| 3,5-(OC₄H₉)₂ | O |
| 3-C₄H₉ | O |
| 4-SC₄H₉ | O |
| 3,5-(CF₃)₂ | S |

For those compounds of Formula I wherein R is —CN, the compounds can be prepared by the reaction, at room temperature, of an appropriate 6-(phenoxy)-picolinaldehyde of the formula

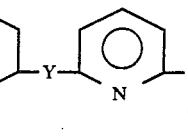

(Formula VI)

wherein X, n and Y are as hereinbefore defined with an excess of an alkali metal cyanide in the presence of an alkali metal bisulfite and water.

In carrying out this reaction, a solution of the aldehyde reactant, the bisulfite and water is reacted with a solution of the cyanide in water. The by-products precipitate out and are separated from the mixture. The aqueous mixture which remains is solvent extracted with a solvent such as benzene, pentane, ether, methylene chloride, hexane, or xylene, water washed and dried and the solvent removed by evaporation leaving the desired product.

EXAMPLE III

Cyano(6-(3-fluorophenoxy)-2-pyridine)methanol (also known as 6-(3-fluorophenoxy)α-hydroxy-2-pyridine acetonitrile)

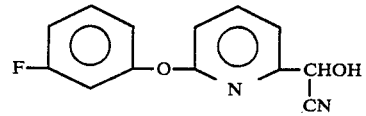

A solution was prepared by mixing 10.6 grams (0.0488 mole) of 6-(3-fluorophenoxy)picolinaldehyde and 5.6 grams (0.0537 mole) of sodium bisulfite in 50 milliliters of water until a solution formed. To this solution was added 2.6 grams (0.0537 mole) of sodium cyanide in 50 milliliters of water. A solid quickly formed and the aqueous mixture which remained was extracted with ether. The ether extract was washed with a 10% sodium bisulfite solution followed by a water wash and dried over magnesium sulfate. The ether was thereafter removed by evaporation. The reaction product was crystallized from hexane to give 12.5 grams of the desired cyano(6-(6-fluorophenoxy)-2-pyridine)methanol product which melted at 73°–74° C. Upon analysis, the product was found to have carbon, hydrogen and nitrogen contents of 63.90, 3.85 and 11.32 percent, respectively, as compared with the theoretical contents of 63.93, 3.71 and 11.47 percent, respectively, calculated for the above-named compound.

By following the preparative procedures as outlined in the above example, the following compounds set forth in Table IV are prepared.

TABLE IV

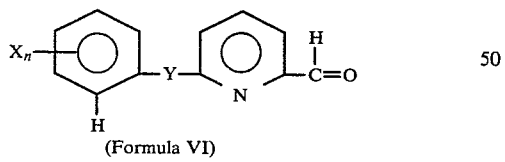

| $X_n$ | Y |
|---|---|
| 3-CH₃ | O |
| 2-CH₃ | O |
| 4-Cl | O |
| 3-CF₃ | S |
| 2-CF₃ | S |
| 4-F | O |
| 4-CH₃ | O |
| H | S |
| H | O |
| 2-Cl; 4-Br | S |
| 3-CH₃; 5-C₄H₉ | O |
| 3-OCH₃; 4-OC₂H₅ | S |
| 2-Cl; 4-CF₃ | O |
| 4-C₂H₅ | O |
| 3-C₂H₅ | O |
| 2-C₂H₅ | S |
| 3-i-C₃H₇ | S |
| 4-Br | O |
| 2,4-Br₂ | S |
| 4-OCH₃ | S |
| 3-OCH₃ | O |
| 2-OCH₃ | O |
| 3-CF₃ | O |
| 2-CF₃ | O |
| 3-i-C₃H₇ | S |
| 2-OC₄H₉ | O |
| 4-OC₄H₉ | S |
| 3,5-(SCH₃)₂ | S |
| 4-SCH₃ | O |
| 3,5-(OC₄H₉)₂ | O |
| 3-C₄H₉ | O |

TABLE IV-continued

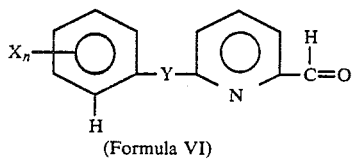

| $X_n$ | Y |
|---|---|
| 4-C$_4$H$_9$ | O |
| 3,5-(CF$_3$)$_2$ | S |

The 6-(phenoxy)picolinaldehydes of the formula

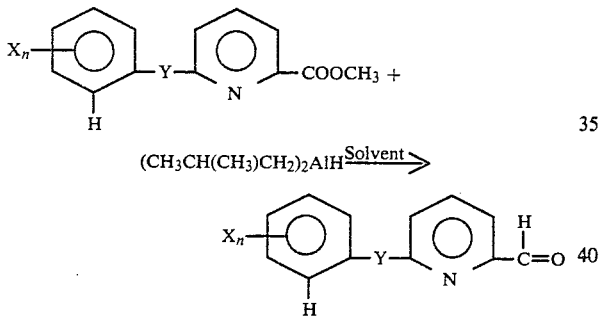

(Formula VI)

wherein X, n and Y are as hereinbefore defined which are employed as starting materials, can be prepared by reacting an appropriate phenoxy or phenylthio pyridine carboxylic acid methyl ester with an excess of diisobutyl aluminumhydride in the presence of a solvent such as, toluene, hexane or xylene. This reaction can be characterized as follows:

wherein X, n and Y are as hereinabove defined.

In carrying out this reaction, the ester reactant is mixed with a solvent under an inert atmosphere and the mixture cooled to below minus (−)50° C. The hydride is slowly added thereto at a temperature below −50° C. Upon completion of the reaction, an acetic acid-water-diethyl ether solution is mixed with the reaction mixture at about −50° C. and the mixture heated slowly to room temperature. The insolubles are removed by filtration and washed with a solvent such as diethyl ether. The filtrate is then followed by a water wash and a wash with sodium bicarbonate and dried. The solvent is removed by evaporation and if desired, the product is further purified by recrystallization from pentane, hexane or benzene and dried.

EXAMPLE IV 6-(3-fluorophenoxy)picolinaldehyde

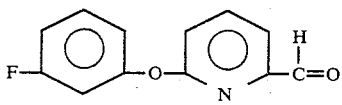

To a stirring mixture of 21.9 grams (0.0849 mole) of 6-(3-fluorophenoxy)methyl picolinate in 150 milliliters of toluene at −50° C. and under a nitrogen atmosphere was slowly added 130 milliliters (0.0121 mole) of diisobutylaluminum hydride (20 percent in hexane) at −50° C. Upon completion of the reaction (as noted by gas-liquid chromatography), 150 milliliters of a solution made from 50 milliliters of acetic acid, 12 milliliters of water and 150 milliliters of ether was slowly added to the reaction mixture at −50° C. The resulting solution was warmed slowly to room temperature. The mixture was thereafter filtered and the filter cake washed thoroughly with ether and the ether solution mixed with the filtrate. The filtrate mixture was washed with water, a sodium bicarbonate solution, dried over anhydrous magnesium sulfate and the ether was removed by evaporation. The 6-(3-fluorophenoxy)picolinaldehyde product remained as a residue and was purified by crystallization from hexane. The product was recovered in a yield of 13.9 grams and melted at 42°–43° C. The structure was confirmed by NMR. Upon analysis, the product was found to have carbon, hydrogen and nitrogen contents of 66.32, 3.92 and 6.21 percent, respectively, as compared with the theoretical contents of 66.36, 3.71 and 6.45 percent, respectively, as calculated for the above-named compound.

By following the preparative procedures as outlined above, employing the appropriate picolinate reactant, the following compounds set forth in Table V are prepared.

TABLE V

| $X_n$ | Y |
|---|---|
| 3-CH$_3$ | O |
| 2-CH$_3$ | O |
| 4-Cl | O |
| 3-CF$_3$ | S |
| 2-CF$_3$ | S |
| 4-F | O |
| H | S |
| H | O |
| 4-CH$_3$ | O |
| 4-C$_2$H$_5$ | O |
| 3-C$_2$H$_5$ | O |
| 2-C$_2$H$_5$ | S |
| 3-i-C$_3$H$_7$ | S |
| 4-Br | O |
| 2,4-Br$_2$ | S |
| 2-Cl; 4-Br | S |
| 4-OCH$_3$ | S |
| 3-OCH$_3$ | O |
| 2-OCH$_3$ | O |
| 3-CF$_3$ | O |
| 2-CF$_3$ | O |
| 3-i-C$_3$H$_7$ | S |
| 2-OC$_4$H$_9$ | O |
| 4-OC$_4$H$_9$ | S |
| 3,5-(SCH$_3$)$_2$ | S |
| 4-SCH$_3$ | O |
| 4-SO$_2$CH$_3$ | O |
| 3,5-(OC$_4$H$_9$)$_2$ | O |
| 3-CH$_3$; 5-C$_4$H$_9$ | O |
| 3-OCH$_3$; 4-OC$_2$H$_5$ | S |
| 2-Cl; 4-CF$_3$ | O |
| 3-C$_4$H$_9$ | O |
| 4-SC$_4$H$_9$ | O |
| 3,5-(CF$_3$)$_2$ | S |

EXAMPLE V 3-(2,2-Dichloroethenyl)-2,2-dimethylcyclopropane carboxylic acid:cyano(6-phenoxy-2-pyridinyl)methyl ester

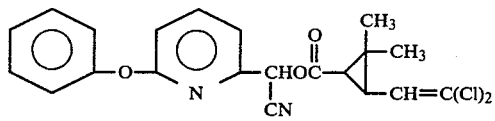

To a cooled solution (10°–15° C.) of 2.0 grams (0.009 mole) of cyano(6-phenoxy-2-pyridine)methanol and 2.0 grams (0.009 mole) of 2,2-dimethyl-3-(2,2-dichloroethenyl)cyclopropane carboxylic acid chloride in 25 milliliters of anhydrous ether was added 1 milliliter of triethylamine. A white precipitate separated out immediately. The reaction mixture was stirred at room temperature for one-half (½) hour. The mixture was diluted with 50 milliliters of water and extracted thoroughly with ether. The ether extract was washed with water, dried over anhydrous magnesium sulfate and concentrated under vacuo to give 3.4 grams of crude 3-(2,2-dichloroethenyl)-2,2-dimethylcyclopropane carboxylic acid:cyano(6-phenoxy-2-pyridinyl)methyl ester product as a thick brown oil. This oil was purified by distillation under reduced pressure to give 1.8 grams of a light brown oil boiling at 190°–200° C. at 0.1–0.2 milliliters of mercury (mm). The oil had a refractive index of $n_D^{25} = 1.5264$. The structure of the product was confirmed by its nuclear magnetic resonance spectrum (NMR). Upon analysis, the product was found to have carbon, hydrogen and nitrogen contents of 60.28, 4.47 and 6.62 percent, respectively, as compared with the theoretical contents of 60.44, 4.35 and 6.71 percent respectively, as calculated for the above compound. (Compound No. 1).

By following the preparative procedure outlined in Example 1 and employing the appropriate cis- or trans-isomer of 2,2-dimethyl-3-(2,2-dichloroethenyl)cyclopropane carboxylic acid chloride, the following compounds were prepared.

Trans-3-(2,2-dichloroethenyl)-2,2-dimethylcyclopropane carboxylic acid:cyano(6-phenoxy-2-pyridinyl)methyl ester having a refractive index of $n_D^{25} = 1.5628$ and carbon, hydrogen and nitrogen contents of 60.28, 4.45 and 6.47 percent respectively, as compared with the theoretical contents of 60.44, 4.35 and 6.71 percent, respectively, as calculated for the above-named compound (Compound 1A); and Cis-3-(2,2-dichloroethenyl)-2,2-dimethylcyclopropane carboxylic acid:cyano(6-phenoxy-2-pyridinyl)methyl ester having a refractive index of $n_D^{25} = 1.5640$ and carbon, hydrogen and nitrogen contents of 60.12, 4.32 and 6.37 percent, respectively as compared with the theoretical contents of 60.44, 4.35 and 6.71 percent, respectively, as calculated for the above-named compound (Compound 1B).

The structure of both of the above compounds was confirmed by (NMR).

EXAMPLE VI 2-(2,2-Dichloroethenyl)-2,2-dimethylcyclopropane carboxylic acid:(6-phenoxy-2-pyridinyl)methyl ester

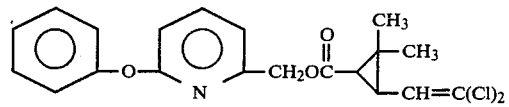

A solution was prepared by dissolving 1.6 grams (0.008 mole) of 6-(phenoxy)picolinalcohol and 1 milliliter of triethylamine in ~25 milliliters of dry ether. The solution was cooled to ~10° and 1.93 grams (0.0085 mole) of 2,2-dimethyl-3-(2,2-dichloroethenyl)cyclopropane carboxylic acid chloride was added thereto, with agitation. The reaction mixture was allowed to sit at 10°–15° for ~4 hours. The mixture was poured into 50 milliliters of water and the organic phase, which separated, was removed and dried with ether. The ether was removed by evaporation and the 3-(2,2-dichloroethenyl)-2,2-dimethylcyclopropane carboxylic acid:(6-phenoxy-2-pyridinyl)methyl ester was recovered as a pale ivory liquid in a yield of 1.7 grams by distillation under reduced pressure. The product had a refractive index of 1.5633 and the structure of the product was confirmed by NMR (Compound No. 2).

EXAMPLE VII 3-(2,2-Dichloroethenyl)-2,2-dimethylcyclopropane carboxylic acid:cyano(6-(3-fluorophenoxy)-2-pyridinyl)methyl ester

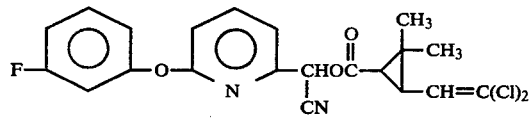

To a solution of 2.1 grams (0.086 mole) of cyano(6-(3-fluorophenoxy)-2-pyridine)methanol and 2.0 grams (0.0088 mole) of 2,2-dimethyl-3-(2,2-dichloroethenyl)-cyclopropane carboxylic acid chloride in 50 milliliters of anhydrous ether was added 3 milliliters of triethylamine. A white precipitate separated out immediately. The reaction mixture was stirred at room temperature for one-half (½) hours. The mixture was successively washed with water, dilute hydrochloric acid, dilute sodium hydroxide, dilute sodium bisulfite, dilute hydrochloric acid and water and thereafter dried over anhydrous magnesium sulfate and concentrated under vacuo to give 3.5 grams of crude 3-(2,2-dichloroethenyl)-2,2-dimethylcyclopropane carboxylic acid:cyano(6-(3-fluorophenoxy)-2-pyridinyl)methyl ester product as a residue. This residue was purified by distillation under reduced pressure to give 3.2 grams of a viscous yellow oil having a refractive index of $n_D^{25} = 1.5538$. The structure of the product was confirmed by its nuclear magnetic resonance spectrum (NMR). In addition, upon analysis, the product was found to have carbon, hydrogen and nitrogen contents of 57.91, 3.95 and 6.16 percent, respectively, as compared with the theoretical contents of 57.94, 3.94 and 6.44 percent, respectively, as calculated for the above-named compound (Compound No. 3).

EXAMPLE VIII 3-(2,2-Dichloroethenyl)-2,2-dimethylcyclopropane carboxylic acid:cyano(6-(3-methoxyphenoxy)-2-pyridinyl)methyl ester

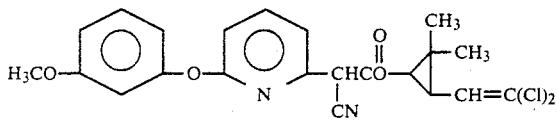

To a solution of 3.0 grams (0.012 mole) of cyano(6-(3-methocyphenoxy)-2-pyridine)methanol and 2.8 grams (0.012 mole) of 2,2-dimethyl-3-(2,2-dichloroethenyl)cyclopropane carboxylic acid chloride in 30 milliliters of anhydrous ether was added dropwise 2.4 grams (0.024 mole) of triethylamine. A white precipitate separated out immediately. The reaction mixture was stirred at room temperature for 2 hours. The mixture was diluted with 50 milliliters of water and extracted thoroughly with ether (2-portions of 50 milliliters each). The ether extract was washed with 100 milliliters of saturated sodium bicarbonate solution, dried over anhydrous magnesium sulfate and the solvent removed by evaporation under reduced pressure. The crude 3-(2,2-dichloroethenyl)-2,2-dimethylcyclopropane carboxylic acid:-cyano(6-(3-methoxyphenoxy)-2-pyridinyl)methyl ester product was recovered as a residue and was a viscous golden oil. This oil was purified by distillation under reduced pressure to give 4.8 grams of a golden oil having a refractive index of $n_D^{25}=1.5627$. The structure of the product was confirmed by its nuclear magnetic resonance spectrum (NMR). Upon analysis, the product was found to have carbon, hydrogen and nitrogen contents of 58.82, 4.58 and 5.90 percent, respectively, as compared with the theoretical contents of 59.07, 4.51 and 6.26 percent, respectively, as calculated for the above-named compound (Compound No. 4).

EXAMPLE IX 2-(2,2-Dichloroethenyl)-2,2-dimethylcyclopropane carboxylic acid:ethynyl(6-phenoxy-2-pyridinyl)methyl ester

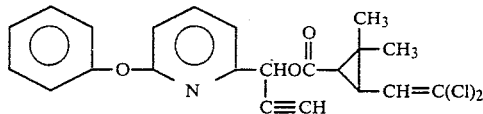

A solution was prepared by bubbling into 100 milliliters of tetrahydrofuran, at 5°-7° C., purified acetylene for 15 minutes. To this solution was added dropwise 10 milliliters of a 2.9 molar (29 millimoles) solution of methyl magnesium bromide in 40 milliliters of tetrahydrofuran and the acetylene addition was continued for an additional ½ hour. To this solution was added 5 grams (25 millimoles) of 6-(phenoxy)picolinaldehyde. The acetylene was stopped and the mixture warmed to room temperature and held there for 3 hours. The reaction mixture was poured into ice water and the precipitate which formed was redissolved by treatment of the mixture with dilute hydrochloric acid. The mixture was extracted with methylene chloride and the extract washed with water, dried and the methylene chloride removed by evaporation. The α-ethynyl-6-phenoxy-2-pyridine methanol product was recovered as a residue in a yield of 7 grams. This product was not purified and was mixed, at room temperature, with 100 milliliters of methylene chloride, 6 grams (26 millimoles) of 2,2-dimethyl-3-(2,2-dichloroethenyl)cyclopropane carboxylic acid chloride and 5 milliliters of triethylamine and stirred overnight. The reaction mixture was sequentially washed with water, 5 percent hydrochloric acid, 5 percent sodium hydroxide, 5 percent sodium bisulfate, 5 percent hydrochloric acid and water. The reaction mixture was thereafter dried over magnesium sulfate and the methylene chloride removed by evaporation. The crude 2-(2,2-dichloroethenyl)-2,2-dimethylcyclopropane carboxylic acid:ethynyl(6-phenoxy-2-pyridinyl)methyl ester was recovered as a residue and purified by elution twice through a chromatograph employing a 2.5 percent solution of acetone in hexane. The cis-isomer, a viscous yellow oil, was recovered as a first fraction in a yield of 1 gram and had a refractive index of $n_D^{25}=1.5671$. Upon analysis, the isomer was found to have carbon, hydrogen and nitrogen contents of 63.37, 4.69, and 3.40 percent, respectively, as compared with the theoretical contents of 63.47, 4.60 and 3.36 percent, respectively, as calculated for the above-named compound. The trans-isomer was recovered as a second fraction and solidified. This material was recrystallized from hexane as a white powder and was recovered in a yield of 1 gram. This product melted at 106°-107° C. and upon analysis was found to have carbon, hydrogen and nitrogen contents of 63.49, 4.57 and 3.37 percent respectively, as compared with the theoretical contents of 63.47, 4.60 and 3.36 percent, respectively, as calculated for the above-named structure (Compound No. 5).

By following the preparative procedures as outlined in the above examples, the following compounds set forth below in Table VI are prepared.

TABLE VI

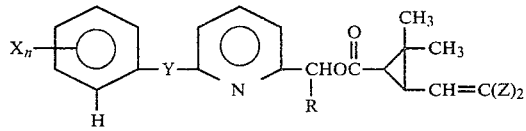

| Compound Number | $X_n$ | Y | R | Z | Molecular Weight | Refractive Index $n_D^{25}$ | Calculated C | Calculated H | Calculated N | Found C | Found H | Found N |
|---|---|---|---|---|---|---|---|---|---|---|---|---|
| 6 | 3-CH₃ | O | —CN | Cl | 431.31 | 1.5610 | 61.26 | 4.67 | 6.50 | 61.37 | 4.81 | 6.58 |
| 7 | 2-CH₃ | O | —CN | Cl | 431.31 | 1.5602 | 61.26 | 4.67 | 6.50 | 61.42 | 4.83 | 6.51 |
| 8 | 4-Cl | O | —CN | Cl | 451.74 | 1.5687 | 55.83 | 3.79 | 6.20 | 55.63 | 3.83 | 5.97 |
| 9 | 3-CF₃ | S | —CN | F | 468.45 | | | | | | | |

TABLE VI-continued

Structure: $X_n$—(phenyl with H)—Y—(pyridine, N)—CHOC(=O)—C(CH$_3$)$_2$—CH=C(Z)$_2$ (cyclopropane), with R on the CHOC carbon.

| Compound Number | $X_n$ | Y | R | Z | Molecular Weight | Refractive Index $n_D^{25}$ | Calculated C | Calculated H | Calculated N | Found C | Found H | Found N |
|---|---|---|---|---|---|---|---|---|---|---|---|---|
| 10 | 3-CF$_3$ | S | —H | F | 443.44 | | | | | | | |
| 11 | 3-CF$_3$ | O | —CN | Cl | 485.29 | 1.5311 | 54.43 | 3.51 | 5.77 | 54.19 | 3.63 | 5.49 |
| 12 | 2-CF$_3$ | O | —C≡CH | Cl | 484.31 | | | | | | | |
| 13 | 4-F | O | —CN | Cl | 435.28 | 1.5529 | 57.94 | 3.94 | 6.44 | 57.83 | 4.02 | 6.10 |
| 14 | 4-CH$_3$ | O | —CN | Cl | 431.31 | 1.5601 | 61.26 | 4.67 | 6.50 | 61.15 | 4.74 | 6.38 |
| 15 | 4-C$_2$H$_5$ | O | —CN | Cl | 445.34 | 1.5491 | 62.02 | 4.94 | 6.29 | 60.44 | 5.08 | 5.46 |
| 16 | 3-C$_2$H$_5$ | O | —CN | Cl | 445.34 | 1.5568 | 62.03 | 4.98 | 6.29 | 62.10 | 5.04 | 6.16 |
| 17 | 2-C$_2$H$_5$ | S | —C≡CH | F | 428.53 | | | | | | | |
| 18 | 3-i-C$_3$H$_7$ | S | —H | Br | 530.36 | | | | | | | |
| 19 | 3-i-C$_3$H$_7$ | O | —CN | Cl | 459.38 | 1.5545 | 62.75 | 5.27 | 6.10 | 62.85 | 5.34 | 5.61 |
| 20 | 4-Br | O | —CN | Cl | 460.74 | 1.5782 | 50.83 | 3.45 | 5.65 | 50.85 | 3.52 | 5.54 |
| 21 | 2,4-Br$_2$ | S | —H | Br | 655.06 | | | | | | | |
| 22 | — | S | —CN | Cl | 433.36 | 1.5913 | 58.20 | 4.19 | 6.46 | 58.21 | 4.29 | 6.45 |
| 23 | 4-OCH$_3$ | S | —H | Br | 528.30 | | | | | | | |
| 24 | 2-OCH$_3$ | O | —CN | F | 412.40 | | | | | | | |
| 25 | 3,4-methylenedioxy | O | —CN | Cl | 459.33 | 1.5719 | 57.27 | 3.90 | 6.07 | 56.36 | 4.12 | 6.10 |
| 26 | 2-OC$_4$H$_9$ | O | —CN | Cl | 489.40 | | | | | | | |
| 27 | 4-OC$_4$H$_9$ | S | —CN | Br | 594.38 | | | | | | | |
| 28 | 4-OC$_4$H$_9$ | O | —CN | Cl | 489.40 | 1.5505 | 61.36 | 5.36 | 5.73 | 61.60 | 5.45 | 5.69 |
| 29 | 3,4-(CH$_3$)$_2$ | O | —H | F | 387.43 | | | | | | | |
| 30 | 3,5-(CH$_3$)$_2$ | O | —CN | Cl | 445.34 | 1.5573 | 62.03 | 4.98 | 6.29 | 62.09 | 5.01 | 5.97 |
| 31 | — | O | —C≡CH | Cl | 416.31 | | | | | | | |
| 32 | 2-F | O | —CN | Cl | 435.28 | 1.5536 | 57.94 | 3.94 | 6.44 | 57.74 | 4.09 | 6.22 |
| 33 | 4-SCH$_3$ | O | —CN | Cl | 463.39 | 1.5870 | 57.02 | 4.32 | 6.05 | 57.06 | 4.47 | 5.92 |
| 34 | 3,4-(CH$_3$)$_2$ | O | —CN | Cl | 445.35 | 1.5608 | 62.03 | 4.98 | 6.29 | 62.14 | 5.06 | 6.01 |
| 35 | 4-OCH$_3$ | O | —CN | Cl | 447.32 | 1.5645 | 59.06 | 4.47 | 6.26 | 59.19 | 4.59 | 6.02 |
| 36 | 3,5-(SCH$_3$)$_2$ | S | —C≡CH | F | 491.65 | | | | | | | |
| 37 | 3-CH$_3$; 5-C$_4$H$_9$ | O | —CN | Cl | 455.43 | | | | | | | |
| 38 | 3,5-(OC$_4$H$_9$)$_2$ | O | —H | Cl | 524.49 | | | | | | | |
| 39 | — | O | —CN | F | 384.39 | | | | | | | |
| 40 | 3-t-C$_4$H$_9$ | O | —CN | Cl | 473.40 | 1.5548 | 63.41 | 5.53 | 5.92 | 63.20 | 5.58 | 5.55 |
| 41 | 3-BR | O | —CN | Cl | 496.20 | 1.5766 | 50.83 | 3.45 | 5.65 | 50.50 | 3.60 | 5.49 |
| 42 | 2-OCH$_3$ | O | —CN | Cl | 447.32 | 1.5621 | 59.07 | 4.51 | 6.26 | 58.48 | 4.57 | 5.98 |
| 43 | 4-SC$_4$H$_9$ | O | —CN | Br | 594.38 | | | | | | | |
| 44 | 3-Cl | O | —CN | Cl | 451.74 | 1.5673 | 55.83 | 3.79 | 6.20 | 55.71 | 3.84 | 5.98 |
| 45 | 3,5-(CF$_3$)$_2$ | S | —CN | F | 520.38 | | | | | | | |
| 46 | 3,5-(CF$_3$)$_2$ | S | —H | F | 511.44 | | | | | | | |
| 47 | 3,5-(OC$_4$H$_9$)$_2$ | O | —CN | Cl | 561.51 | | | | | | | |
| 48 | 2-CF$_3$ | O | —C≡CH | Br | 641.22 | | | | | | | |
| 49 | 4-SC$_4$H$_9$ | O | —CN | Cl | 505.45 | 1.5718 | 59.40 | 5.19 | 5.54 | 59.47 | 5.21 | 5.01 |
| 50* | 4-SO$_2$CH$_3$ | O | —CN | Cl | 495.39 | | 53.34 | 4.07 | 5.66 | 53.85 | 4.42 | 5.06 |
| 51 | 4-SO$_2$C$_4$H$_9$ | O | —CN | Cl | 537.47 | | | | | | | |
| 52 | 2-Cl; 4-Br | S | —H | Br | 575.15 | | | | | | | |
| 53 | 2-Cl; 4-CF$_3$ | O | —CN | Cl | 505.73 | | | | | | | |
| 54 | 3-OCH$_3$; 4-OC$_2$H$_5$ | S | —CN | Cl | 477.37 | | | | | | | |
| 55 | 2-CH$_3$; 4-Cl | O | —CN | Cl | 453.76 | 1.5649 | 56.71 | 4.08 | 6.02 | 57.15 | 4.23 | 5.84 |
| 56 | 3-CH$_3$; 4-Cl | O | —CN | Cl | 453.76 | 1.5720 | 56.71 | 4.08 | 6.02 | 56.93 | 4.0 | 5.72 |
| 57 | 3,4-Cl$_2$ | O | —CN | Cl | 486.19 | 1.5795 | 51.85 | 3.29 | 5.76 | 52.06 | 3.12 | 5.40 |
| 58 | 3,5-Cl$_2$ | O | —CN | Cl | 486.19 | 1.5785 | 51.85 | 3.29 | 5.76 | 52.07 | 3.06 | 5.34 |
| 59 | — | O | —C≡CH | Br | 505.22 | | | | | | | |
| 60 | — | S | —C≡CH | Cl | 432.37 | | | | | | | |
| 61 | 4-Cl | O | —C≡CH | Cl | 450.75 | | | | | | | |
| 62 | 4-F | O | —C≡CH | Cl | 434.30 | | | | | | | |
| 63 | 4-F | S | —C≡CH | F | 417.45 | | | | | | | |
| 64 | 3-Cl | O | —C≡CH | Cl | 450.75 | | | | | | | |
| 65 | 4-OCH$_3$ | O | —C≡CH | Cl | 446.33 | | | | | | | |
| 66 | 4-CH$_3$ | O | —C≡CH | Cl | 430.33 | | | | | | | |
| 67 | 4-CH$_3$ | S | —C≡CH | Br | 535.31 | | | | | | | |
| 68 | — | O | H | Cl | 392.29 | | | | | | | |
| 69 | — | O | H | F | 359.38 | | | | | | | |
| 70 | 4-Cl | O | H | Cl | 426.73 | | | | | | | |
| 71 | 4-F | O | H | Cl | 410.28 | | | | | | | |
| 72 | 3-Cl | O | H | Cl | 426.73 | | | | | | | |
| 73 | 4-OCH$_3$ | O | H | Cl | 399.26 | | | | | | | |
| 74 | 4-CH$_3$ | O | H | Cl | 392.29 | | | | | | | |
| 75 | 4-CH$_3$ | S | H | Br | 497.26 | | | | | | | |
| 76 | 4-Cl | S | H | F | 409.89 | | | | | | | |
| 77 | 3-Cl | S | H | Br | 531.71 | | | | | | | |
| 78 | 4-F | S | H | Br | 515.25 | | | | | | | |

TABLE VI-continued

Structure: Xn-[phenyl]-Y-[pyridine with N-H]-CH(R)-O-C(=O)-C(CH3)2-CH=C(Z)2

| Compound Number | Xn | Y | R | Z | Molecular Weight | Refractive Index $n_D^{25}$ | Calculated C | H | N | Found C | H | N |
|---|---|---|---|---|---|---|---|---|---|---|---|---|
| 79 | 4-OCH$_3$ | S | H | F | 382.41 | | | | | | | |

*Compound has melting point of 112°–114° C.

As indicated hereinabove, the substituted pyridine methyl esters of cyclopropane carboxylic acid possess insecticidal properties. The compounds have quick knockdown activity and low persistence, as toxic residues, and have low mammalian toxicity.

Because of the "quick knockdown", the subject compounds are particularly suitable for the control, inside houses, barns, warehouses, public buildings, and the like, of pests, including cockroaches, such as the German cockroach, American cockroach, and brown-banded cockroach; beetles, such as the black-carpet beetle, confused flour beetle, saw-tooth grain beetle, and larder beetle, spiders, silverfish, bedbugs; fleas such as those on bedding used by household pets, and flea larvae; mosquitos; boxelder bugs; spiders; mites; ants; centipedes; and flies, such as hornfly, stable fly and facefly and the common housefly. The subject compounds are highly effective for such indoor control of insect pests and thus are particularly adapted for such employment. In addition, the subject compounds are also useful for the control of lice and ticks and other insects parasitic to animals.

The new compounds of the present invention are very effective for the control of the many insect pests found on the roots or aerial portions of growing plants, including aphids, scale, mites, and chewing and sucking insects, such as leafhopper, Southern army worm, two-spotted spider mite, cotton aphid, cabbage looper, western spotted cucumber beetle, bollworm, codling moth, beet armyworm, and tobacco budworm.

The subject compounds, when applied to plants, plant parts, and their habitats to protect the plants from the attack of insect pests, exhibit residual control of the insects over only a relatively short period of time thereby not having appreciable build-up in the environment.

In some procedures, the compounds can be vaporized or sprayed or distributed as aerosols into the air, or onto surfaces in contact with the air. In such applications, the compounds manifest the useful properties hereinbefore described.

The methods of the present invention comprise contacting an insect with an insecticidally effective or inactivating amount of one of the compounds of the present invention.

The contacting can be effected by application of the compound to the habitat of the insects. Representative habitats include soil, air, water, food, vegetation, inert objects, stored matter such as grains, other animal organisms, and the like. The inactivation can be lethal, immediately, or with delay, or can be a sub-lethal, one in which the inactivated insect is not able to carry out one or more of its normal life processes. This latter situation prevails when one of the systems of the insect, typically the nervous system, is seriously disturbed. A preferred embodiment of the present invention comprises the employment of the present method for the kill and control of insects; such employment gives excellent results, particularly in control of insects that have developed resistance against other pest-control substances.

The inactivation of an insect by the application of an insecticidally effective or inactivating amount of one of the presently claimed compounds is critical to the method of the present invention. The compound can sometimes be employed in unmodified form. Frequently, however, for easier application, the compound is modified by the employment with it of a pesticidal adjuvant or inert carrier therefor. Thus, for example, the present compounds are of very low solubility in water but are relatively soluble in oils, including plant essential oils. Therefore, the practical enjoyment of the beneficial utilities of the present compounds often requires that the compound be composited with one or more pesticidal adjuvant substances, and the resulting compositions are comprehended within the present invention.

The compositions can be formulated in various forms, such as emulsifiable concentrates, wettable powders, flowable suspension dusts, granules, microencapsulated granules, fine granules, oil sprays, aerosols, heating fumigants (e.g. mosquito coils, electric mosquito killer mat, etc.), fogging mists, non-heating fumigants and poisonous baits and the adjuvant employed can be any one or a plurality of materials including aromatic solvents, petroleum distillates, water, or other liquid carriers, propellant substances, surface-active dispersing agents, light absorbers, and finely divided carrier solids. In such compositions, the adjuvant cooperates with the compound so as to obtain a composition to facilitate the method of the present invention, and to obtain an improved result. The use of either a surface-active dispersing agent or a finely divided carrier solid and the use of both a surface-active dispersing agent and a finely divided carrier solid, simultaneously, constitute preferred embodiments of the method of the present invention. Another preferred embodiment of the present invention is a composition comprising one or more of the presently claimed compounds, an organic liquid as a solvent and carrier therefor, and a propellant material. Numerous other embodiments will become available to those skilled in the art in view of the teachings set forth hereinbelow.

The exact concentration of the active compounds in a composition thereof with an adjuvant therefor can vary; it is only necessary that the active compounds be present in a sufficient amount so as to make possible the application of an insecticidally effective or inactivating dosage. Generally, for practical applications, the active compounds can be broadly applied to insect pest organisms or their habitat in compositions containing from about 0.00001 percent to about 98 percent by weight of the active compound.

In the preparation of dust compositions, the product can be compounded with any of the finely divided carrier solids such as pyrophyllite, diatomaceous earth, gypsum and the like. In such operations, the finely divided carrier is ground or mixed with one or more of the active compounds, as active agent, or wetted with a solution of the active agent in a volatile organic solvent. Similarly, dust compositions containing the active product can be similarly compounded from various of the solid dispersing agents, such as fuller's earth, attapulgite and other clays. These dust compositions can be employed as treating compositions or can be employed as concentrates and subsequently diluted with additional solid dispersing agent or with pyrophyllite, diatomaceous earth, gypsum and the like to obtain the desired amount of active agent in a treating composition. Also, such dust compositions can be dispersed in water, with or without the aid of surfactant, to form spray mixtures.

Further, one of the compounds or a dust concentrate composition containing such compound can be incorporated in intimate mixture with surface active dispersing agents such as ionic and nonionic emulsifying agents to form spray concentrates. Such concentrates are readily dispersible in liquid carriers to form sprays containing the toxicant in any desired amount. The choice of dispersing agent and amount thereof employed are determined by the ability of the agent to facilitate the dispersion of the concentrate in the liquid carrier to produce the desired spray composition.

In the preparation of liquid compositions, the compounds of the present invention can be compounded with a suitable water-immiscible organic liquid and surface-active dispersing agent to produce as emulsifiable liquid concentrate which can be further diluted with water and oil to form spray mixtures in the form of oil-in-water emulsions. In such compositions, the carrier comprises an aqueous emulsion, that is, a mixture of water-immiscible solvent, emulsifying agent and water. Preferred dispersing agents to be employed in these compositions are oil-soluble and include the non-ionic emulsifiers such as the polyoxyethylene derivatives of sorbitan esters, complex ether alcohols and the like. However, oil-soluble ionic emulsifying agents such as mahogany soaps can also be used. Suitable organic liquids to be employed in the compositions include petroleum oils and distillates, toluene, liquid halohydrocarbons and synthetic organic oils.

When operating in accordance with the present invention, the compound or a composition containing the compound is applied to the insects to be controlled directly, or by means of application to a portion or portions of their habitat in any convenient manner, for example, by means of hand dusters or sprayers or by simple mixing with the food to be ingested by the organisms. Application to the foliage of plants is conveniently carried out with power dusters, boom sprayers and fog sprayers. In such foliar applications, the employed compositions should not contain any appreciable amounts of any phytotoxic diluents. In large scale operations, dusts, or low-volume sprays can be applied from an airplane. The present invention also comprehends the employment of compositions comprising one of the compounds, an adjuvant, and one or more other biologically active materials, such as insecticides, fungicides, miticides, bactericides, nematocides, and the like.

A preferred and especially convenient matter for the application of one or more of the present products comprises the use of a self-pressurized pack formulation which can be used, for example, as a space of surface spray. Such a formulation can comprise one or more of the compounds, an organic liquid as a solvent and vehicle therefor, and a propellant material which can be a condensed and compressed gas or a substance which, at room temperature, is a gas under atmospheric pressure but which liquifies under superatmospheric pressure. Where the propellant material is of the latter type, the self-pressurized pack formulation is often spoken of as an aerosol. Representative propellants include propane, butane, nitrogen, and the fluorinated hydrocarbons, such as dichlorodifluoromethane and trichlorofluoromethane. Generally, the propellant constitutes from 25 to 95 percent by weight of the total self-pressurized pack. As vehicle, there can be employed any liquid in which the desired amount of product is capable of being dispersed; preferred vehicles include petroleum distillates, kerosene, and methylene chloride. The self-pressurized pack formulation can also include other materials, such as other biologically active agents or synergists. For further discussion of the use of self-pressurized pack formulations, see U.S. Pats. 1,892,750 and 2,321,023.

The compositions of the present invention will be illustrated in further detail below with reference to the examples, but the kinds and mixing proportions of compounds and additives are not limited to those shown in the examples but are variable within wide ranges. In the Examples set forth hereinafter, the compounds employed are referred to by the compound number as hereinabove set forth. All parts are based on weight percent of the total composition.

EXAMPLE X

A dust composition is prepared by admixing and pulverizing 3 parts of one of the compounds numbered 2, 3, 4, 8, 9, 11, 16, 17, 22, 23, 26, 36, 53 or 54 with 97 parts of Barden clay to obtain a composition containing 3 percent of the active ingredient. In application, the composition is dusted as such.

EXAMPLE XI

50 Parts of one of the compounds numbered 35, 54 or 55; 5 parts of a wetting agent (alkylbenzenesulfonate type) and 45 parts of diatomaceous earth are thoroughly pulverized and mixed together to obtain a wettable powder containing 50 percent of active ingredient. In application, the powder is diluted with water and used as a spray.

EXAMPLE XII

A mixture of 5 parts of one of the compounds numbered 2, 5, 7, 13, 43, 44, 51, 54 or 55; 93.5 parts of clay and 1.5 parts of polyvinyl alcohol are thoroughly kneaded with water and the mixture granulated and dried. The granule composition contains 5 percent of the active ingredient and can be applied as such.

EXAMPLE XIII

25 Parts of compound numbered 49, 50 parts of toluene and 25 parts of Atlox 3404F ® (proprietary material of Imperial Chemical Industries, U.S. which is a polyoxyethylene alkyl aryl ether-alkyl aryl sulfonate blend) are mixed together to obtain an emulsifiable concentrate having an active ingredient concentration of 25 percent. In application, the concentrate is diluted with water and sprayed.

EXAMPLE XIV 7.6 Parts of one of the compounds numbered 17, 20, 46, 48, 50, 51 or 54; 80.4 parts of a polyoxyethylene sorbitol ester emulsifier are mixed together to obtain an emulsifiable concentrate having an active ingredient concentration of 7.6%. In application, the preparation is diluted with water and used as a spray.

EXAMPLE XV

1 Part of one of the compounds numbered 8, 11, 16, 37, 42 or 44 is mixed with 99 parts of purified Kerosene to obtain an oil preparation having an active ingredient concentration of 1 percent. In application, the composition can be atomized or sprayed as is.

The control of pest organisms by the contacting thereof with one or more of the compounds of the present invention is illustrated by the following examples.

EXAMPLE XVI:

Cylindrical cages about $3\frac{5}{8}$ inches in diameter by $3\frac{1}{4}$ inches high were fitted with wire screen on the top and bottom. Into each cage was placed a predetermined number of German cockroaches. An aqueous dispersion, prepared by admixing one of the hereinafter set forth compounds with a predetermined amount of water and a surfactant, was sprayed on the cockroaches through the screen from a distance of about 15 inches. At the same time additional cockroaches were sprayed with a water-surfactant mixture containing no active toxicant to serve as controls. After spraying, the cockroaches were fed a sugar-water diet for 3 days. At the end of this period, the cages were examined to determine the minimum concentration in parts of active compound per million parts of the ultimate composition (PPM) necessary to give at least a 100 percent ($LD_{100}$) kill and control of the cockroaches. The results of this examination are set forth below in Table VII.

TABLE VII

| Compound Number of Active Compound | Minimum Concentration of Active Compound in PPM to Give $LD_{100}$ for German Cockroaches |
| --- | --- |
| 1 | 25 |
| 1A | 50 |
| 1B | 25 |
| 3 | 25 |
| 4 | 400 |
| 6 | 25 |
| 7 | 25 |
| 11 | 400 |
| 13 | 25 |
| 14 | 100 |
| 15 | 25 |
| 16 | 100 |
| 25 | 25 |
| 32 | 25 |
| Control | — |

EXAMPLE XVII

An aqueous dispersion was prepared by dispersing a predetermined amount of one of the test compounds and a predetermined amount of a surfactant in a predetermined amount of water. At the same time, a water/surfactant mixture containing none of the compounds was also prepared to serve as a control. Sheets containing egg masses of codling moths are pinned to apples and the egg sheets and apples are drenched with an aqueous dispersion of one of the hereinafter set forth compounds. Separate egg masses on apples were also treated with the control mixture. The egg masses/apples were incubated under conditions conducive to the hatching of the eggs and the growth of the larvae therefrom. Ten days after treatment, the apples were examined for the presence of larvae. Counts of the number of larvae penetration in the treated fruit was compared to the number present in the control to determine the present control obtained with the test compounds.

This examination determined the minimum concentration in parts of the active compound per million parts of the ultimate dispersion necessary to give at least a 70 percent kill and control of codling moth larvae and the results of this examination are set forth below in Table VIII.

TABLE VIII

| Number of Active Compound | Minimum Concentration in PPM of Active Compound in Aqueous Dispersion to give $LD_{70}$ for Codling Moth Larvae |
| --- | --- |
| 1 | 25 |
| 3 | 25 |
| 5 | 25 |
| 6 | 100 |
| 11 | 100 |
| 13 | 25 |
| 14 | 25 |
| 15 | 25 |
| 16 | 25 |
| 25 | 100 |
| 33 | 400 |
| 34 | 25 |
| 35 | 25 |
| Control | — |

EXAMPLE XVIII

Seventy-five grams of air-dried soil was placed in an 8-ounce container. To the soil was added a predetermined amount of an aqueous dispersion prepared by admixing a predetermined amount of one of the hereinafter set forth compounds with a predetermined amount of water and a predetermined amount of a surfactant, to give various predetermined concentrations of the toxicant in the soil on a soil-chemical basis. The treated soil was air-dried and thoroughly mixed by agitation. To each treated container, and control containers treated with water and surfactant alone, was added 0.5 milliliters of an aqueous suspension of the eggs of the Western spotted cucumber beetle (WSCB) (70–80 eggs of 3–4 days old). Additional treated soil was used to cover the eggs and corn seed was placed on the soil and covered with additional treated soil. The containers were thereafter maintained under conditions conductive to the growth of the seeds and the hatching of the eggs. Twelve (12) days after treatment, the containers and the plants therein were examined to determine the minimum concentration in parts of active compound per million parts of the ultimate dispersion necessary to give at least a 100 percent kill and control of the larvae from the hatched eggs. The results of this examination are set forth below in Table IX.

TABLE IX

| Number of Active Compound | Minimum Concentration in PPM of Active Compound in Soil to give a LD$_{100}$ of WSCB Larvae |
| --- | --- |
| 1 | 6 |
| 3 | 6 |
| 6 | 6 |
| 13 | 25 |
| 14 | 6 |
| 15 | 25 |
| 25 | 25 |
| 32 | 6 |
| 33 | 6 |
| 34 | 1.5 |
| 35 | 25 |
| Control | — |

EXAMPLE XIX

In this operation, aqueous dispersions were prepared by admixing one of the hereinafter set forth compounds with a predetermined quantity of water and a predetermined amount of a surfactant to give aqueous dispersions containing varying predetermined amounts of one of the compounds as the sole active toxicant. Separate cotton plant leaves were thoroughly wetted briefly with one of the dispersions and the wetted leaves placed in an open petri dish and permitted to dry. After the leaves were dry, 5 live beet armyworm larvae were placed in each Petri dish. In identical operations, 5 live geet armyworm larvae were placed in control Petri dishes, the leaf therein having been wetted with a solution containing only water and surfactant. The dishes were maintained under moist conditions conducive for the growth of the beet armyworm larvae for a period of about 5 days. At the end of the 5-day period, the dishes were examined to determine the minimum concentration in parts of the active compound per million parts of the ultimate dispersion necessary to give at least a 100 percent kill and control of the beet armyworm larvae. The results of this examination are set forth below in Table X.

TABLE X

| Number of Active Compound | Minimum Concentration in PPM of Active Compound in Dispersion to give LD$_{100}$ for beet Armyworm Larvae |
| --- | --- |
| 1 | 25 |
| 1A | 50 |
| 1B | 12.5 |
| 3 | 25 |
| 6 | 100 |
| 7 | 100 |
| 11 | 400 |
| 13 | 25 |
| 14 | 100 |
| 15 | 100 |
| 16 | 100 |
| 19 | 100 |
| 25 | 100 |
| 32 | 25 |
| 33 | 400 |
| 34 | 400 |
| 35 | 100 |
| Control | — |

EXAMPLE XX

In this operation, aqueous dispersions were prepared by admixing one of the hereinafter set froth compounds with a predetermined quantity of water and a predetermined amount of a surfactant to give aqueous dispersions of varying predetermined amounts of one of the compounds as the sole active toxicant. Separate 3 inch discs cut from tobacco plant leaves were thoroughly wetted briefly with one of the dispersions and the wetted leaves placed in an open Petri dish and permitted to dry. After the leaves were dry, 5 live tobacco budworm larvae were placed in each Petri dish. In identical operations, 5 live tobacco budworm larvae were placed in Control Petri dishes, the leaf therein having been wetted with a solution containing only water and surfactant. The dishes were maintained under moist conditions conducive for the growth of the tobacco budworm larvae for a period of about 2 days. At the end of the 2-day period, the dishes were examined to determine the minimum concentration in parts of the active compound per million parts of the ultimate dispersion necessary to give at least a 100 percent kill and control of the tobacco budworm larvae. The results of this examination are set forth in Table XI.

TABLE XI

| Number of Active Compound | Minimum Concentration in PPM of Active Compound in Dispersion to give LD$_{100}$ for Tobacco Budworm Larvae |
| --- | --- |
| 1 | 25 |
| 1A | 3.1 |
| 1B | 12.5 |
| 4 | 25 |
| 6 | 100 |
| 7 | 400 |
| 11 | 100 |
| 13 | 25 |
| 14 | 100 |
| 15 | 400 |
| 16 | 400 |
| 25 | 100 |
| 30 | 400 |
| 32 | 100 |
| 33 | 100 |
| 34 | 25 |
| 35 | 100 |
| Control | — |

EXAMPLE XXI

Aqueous dispersions were prepared by admixing one of the hereinafter set forth compounds with a predetermined quantity of water and a predetermined amount of a surfactant to give aqueous dispersions containing varying predetermined amounts of one of the compounds as the sole toxicant. Separate rice plants were dipped into one of the dispersions and permitted to dry. A plastic cylinder was placed around the plants and 10 adult Aster leafhoppers were placed in the cylinder and the cylinder capped. In a like manner, 10 adult Aster leafhoppers were placed on control plants which had been dipped in a solution containing only water and surfactant. The plants were maintained under conditions conducive to the growth of the plants and leafhoppers. After a period of two days, the cylinder and plants were examined to determine the minimum concentration in parts of the active compound per million parts of the ultimate dispersion necessary to give at least 95 percent kill and control of the Aster leafhopper. The results of this examination are set forth below in Table XII.

TABLE XII

| Number of Active Compound | Minimum Concentration in PPM of Active Compound in Dispersion to give LD$_{95}$ for Aster Leafhoppers |
|---|---|
| 1 | 12.5 |
| 1A | 12.5 |
| 1B | 12.5 |
| 4 | 400 |
| 8 | 25 |
| 16 | 100 |
| 20 | 25 |
| 28 | 100 |
| 30 | 400 |
| 34 | 25 |
| 40 | 400 |
| 42 | 400 |
| 44 | 25 |
| 49 | 100 |
| Control | — |

EXAMPLE XXII

Aqueous dispersions were prepared by admixing one of the hereinafter set forth compounds with a predetermined quantity of water and a predetermined amount of a surfactant to give aqueous dispersions containing varying predetermined amounts of one of the compounds as the sole toxicant. Separate wild mustard plants were infested with 20 green peach aphids and the plants sprayed with one of the dispersions to run off. In a like manner, 20 green peach aphids were placed on control plants and the plants sprayed to run off with a solution containing only water and surfactant. The plants were maintained under conditions conducive to the growth of the plants and aphids. After a period of two days, the plants were examined to determine the minimum concentration in parts of the active compound per million parts of the ultimate dispersion necessary to give at least 100 percent kill and control of the green peach aphids. The results of this examination are set forth below in Table XIII.

TABLE XIII

| Number of Active Compound | Minimum Concentration in PPM of Active Compound in Dispersion to give LD$_{100}$ for Green Peach Aphid |
|---|---|
| 1 | 3.1 |
| 1B | 1.5 |
| 8 | 6.25 |
| 13 | 6.25 |
| 35 | 6.25 |
| Control | — |

EXAMPLE XXIII

Aqueous dispersions were prepared by admixing one of the hereinafter set forth compounds with a predetermined quantity of water and a predetermined amount of a surfactant to give aqueous dispersions containing varying predetermined amounts of one of the compounds as the sole toxicant. Separate groups of 5 adult carpet beetles (*Trogoderma versicolor*) were placed on filter paper in a Petri dish and were sprayed with 1 milliliter of one of the test dispersions. At the same time, additional dishes containing 5 adult carpet beetles were sprayed with a water/surfactant mixture containing none of the compounds. The dishes were maintained under conditions conducive to the growth of the beetles. After a period of 24 hours, the Petri dishes were examined to determine the minimum concentration in parts of the active compound per million parts of the ultimate dispersion necessary to give at least 100 percent kill and control of the carpet beetles. The results of this examination are set forth below in Table XIV.

TABLE XIV

| Number of Active Compound | Minimum Concentration in PPM of Active Compound in Dispersion to give LD$_{100}$ for Carpet Beetles |
|---|---|
| 1 | 6.2 |
| 1B | 6.2 |
| 8 | 3.1 |
| 13 | 12.5 |
| 35 | 25 |
| Control | — |

Preparation of Starting Materials

The 2,2-dimethyl-3-(2,2-dihaloethenyl)cyclopropane carboxylic acid halides employed as starting materials in the preparation of the active compounds of the present invention are well known compounds and are taught in prior art references including J. Farkas et al., Chem. Listyl, 52 688 (1958) (Chem. Abst. 52 13650 (1958)); U.S. Pat. No. 3,981,903. In addition, U.S. Pat. Nos. 3,979,519 and 3,981,903 teach the above carboxylic acids as the free acid. These acids can be converted to the acid halide by conventional procedures such as, for example, reacting at a temperature of from about room temperature to about 90° C. the appropriate 2,2-dimethyl-3-(2,2-dihaloethenyl)cyclopropane carboxylic acid with a thionyl halide such as thionyl chloride, thionyl bromide or thionyl fluoride or a phosphorus halide such as phosphorus trichloride or phosphorus oxychloride in the presence of an organic solvent such as benzene, hexane or a benzene-hexane mixture.

In addition, the cis-and trans-isomers of 2,2-dimethyl-3-(2,2-dihaloethenyl)cyclopropane carboxylic acid halides employed as starting materials can be prepared by first separating the corresponding free acid or ethyl ester of the above compound into the respective cis- and trans-isomers by conventional separation techniques, such as the one taught in Burt et al., Pesticide Science, 5, pages 791–799, (1974), hydrolysis of the ester to the acid if such was separated and thereafter converting the acid to the acid halide as taught hereinabove.

What is claimed is:

1. A compound corresponding to the formula

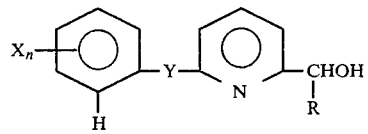

wherein X independently represents alkyl of 1 to 4 carbon atoms, alkoxy of 1 to 4 carbon atoms, alkylthio of 1 to 4 carbon atoms, alkylsulfonyl of 1 to 4 carbon atoms, trifluoromethyl, 3,4-methylenedioxy, chloro, fluoro or bromo; n represents an integer of 0 to 2; Y represents oxygen or sulfur and R represents cyano or ethynyl.

2. A compound as defined in claim 1 wherein Y is oxygen.

3. A compound as defined in claim 1 wherein R is cyano.

4. A compound as defined in claim 2 wherein R is cyano.

5. A compound as defined in claim 4 wherein n is 0.

6. The compound as defined in claim 4 which is cyano(6-phenoxy-2-pyridine)methanol.

7. The compound as defined in claim 4 which is cyano(6-(3-methoxyphenoxy)-2-pyridine)methanol.

8. The compound as defined in claim 4 which is cyano(6-(4-methoxyphenoxy)-2-pyridine)methanol.

9. The compound as defined in claim 4 which is cyano(6-(4-chlorophenoxy)-2-pyridine)methanol.

10. The compound as defined in claim 4 which is cyano(6-(3-fluorophenoxy)-2-pyridine)methanol.

11. The compound as defined in claim 4 which is cyano (6-(4-fluorophenoxy)-2-pyridine)methanol.

12. The compound as defined in claim 2 wherein R is ethynyl.

13. The compound as defined in claim 12 which is α-ethynyl-6-phenoxy-2-pyridine methanol.

* * * * *

UNITED STATES PATENT AND TRADEMARK OFFICE
CERTIFICATE OF CORRECTION

PATENT NO. : 4,256,893

DATED : March 17, 1981

INVENTOR(S) : Sudarshan K. Malhotra et al

It is certified that error appears in the above—identified patent and that said Letters Patent is hereby corrected as shown below:

Col. 19, line 39, "as" should read -- an --.

Col. 20, line 7, "of" should read -- or --.

Col. 22, line 60, "conductive" should read -- conducive.

Col. 23, line 33, "geet" should read -- beet --.

Col. 24, line 4, "froth" should read -- forth --.

Signed and Sealed this

First Day of September 1981

[SEAL]

Attest:

Attesting Officer

GERALD J. MOSSINGHOFF

Commissioner of Patents and Trademarks